United States Patent [19]

Schmidt

[11] Patent Number: 5,594,774
[45] Date of Patent: Jan. 14, 1997

[54] HOLDER FOR RECEIVING A SHEET-LIKE MEDIUM FOR X-RAY IMAGES

[75] Inventor: Manfred Schmidt, Schrobenhausen, Germany

[73] Assignee: AGFA Geavert, Munich, Germany

[21] Appl. No.: 503,106

[22] Filed: Jul. 17, 1995

[30] Foreign Application Priority Data

Aug. 5, 1994 [DE] Germany .......................... 44 27 783.0

[51] Int. Cl.[6] .................................................. G03B 42/02
[52] U.S. Cl. ........................................... 378/177; 378/167
[58] Field of Search ..................................... 378/167, 177

[56] References Cited

U.S. PATENT DOCUMENTS 4,352,197  9/1982  Waerve ..................................... 378/177
5,265,148  11/1993  Bauer et al. .

FOREIGN PATENT DOCUMENTS 3718130  12/1988  Germany .
9005115  9/1990  Germany .
4008778  9/1991  Germany .

Primary Examiner—Craig E. Church
Attorney, Agent, or Firm—Furgang & Milde, LLP

[57] ABSTRACT

A holder (3) for retaining a sheet of X-ray sensitive film (24) for making X-ray pictures includes (1) an outer cassette (5) with a low-friction shape and surface and (2) an inner cassette (20) that can be opened and closed, that is lightproof when closed, and that can be accommodated in the outer cassette. The inside of the closed outer cassette is longer and wider than the film and considerably higher than the film is thick.

13 Claims, 3 Drawing Sheets

HOLDER FOR RECEIVING A SHEET-LIKE MEDIUM FOR X-RAY IMAGES

BACKGROUND OF THE INVENTION

The present invention concerns a holder for retaining a sheet-like, X-ray sensitive medium of the type used in making X-ray pictures.

Such holders are employed for making X-ray exposures on conventional X-ray film or a stimulable phosphor imaging plate. The film is often secured in a holder in the form of a cassette while being exposed. Once the picture has been taken, the sheet-like medium is removed from the cassette for processing. The conventional films are developed conventionally and the phosphor imaging plates are excited, point by point, by a beam of light, usually a laser. The phosphorescence is scanned electro-optically, generating electronic image signals that can be further processed digitally in a computer.

The cassettes are automatically loaded with either type of X-ray sensitive medium by inserting them in a cassette loader. The cassette is loaded inside the loader, which is light-proof, with a fresh film of whatever type is desired. The loaded cassette is then inserted into the X-ray apparatus ready for exposure.

X-rays are employed in many fields, in non-destructive materials testing for example and especially for medical diagnoses. Medical X-ray pictures must be produced rapidly, especially in emergencies. Mobile X-ray apparatus is usually employed for bedridden or wounded patients. Such apparatus is positioned over the patient being radiographed and the loaded cassette is positioned beneath the patient. A bedridden patient accordingly has to be lifted in order to slide the cassette in under him or her. The cassette must then be positioned correctly in relation to the regions being imaged. Experience demonstrates that conventional cassettes are difficult to slide in under a patient and, once there, to position correctly for exposure. The cassette is of course also difficult to remove once the exposure has been made. Cassettes are sometimes severely stressed mechanically by heavy patients, and can even break as a result.

SUMMARY OF THE INVENTION

A principal object of the present invention is to provide a mechanically robust holder for receiving a sheet-like medium which will allow the production of very high-quality X-ray images of subjects that move very little, if at all.

This object, as well as other objects which will become apparent from the discussion that follows, are achieved, in accordance with the present invention, by providing a holder which comprises:

a) an inner cassette that can be opened to receive the sheet-like medium and thereafter closed, the inner cassette being lightproof when closed; and b) an outer cassette having a low-friction shape and surface and having a compartment for holding the inner cassette.

The holder in accordance with the present invention thus comprises two cassettes, one fitting inside the other. The inner cassette can be a conventional X-ray cassette and the outer cassette more or less a cover that protects it. The outer cassette protects the inner cassette mechanically from damage and visually from contamination. Visual protection is particularly important in relation to X-ray pictures needed in medical emergencies because victims are often brought to the hospital covered in blood. The protective outer cassette keeps the sensitive inner cassette clean. Again, since the surface of the outer cassette is very smooth, it is easier to slide in under the subject and to position correctly with respect to the region of interest.

Another advantage of the present invention is that the outer surface of the outer cassette has no sharp edges. It also has finger grips that help to position it beneath the patient. The image can be further improved with a scatter grid.

For a full understanding of the present invention, reference should now be made to the following detailed description of the preferred embodiments of the invention as illustrated in the accompanying drawings.

DESCRIPTION OF THE PREFERRED EMBODIMENTS

Figure 1:
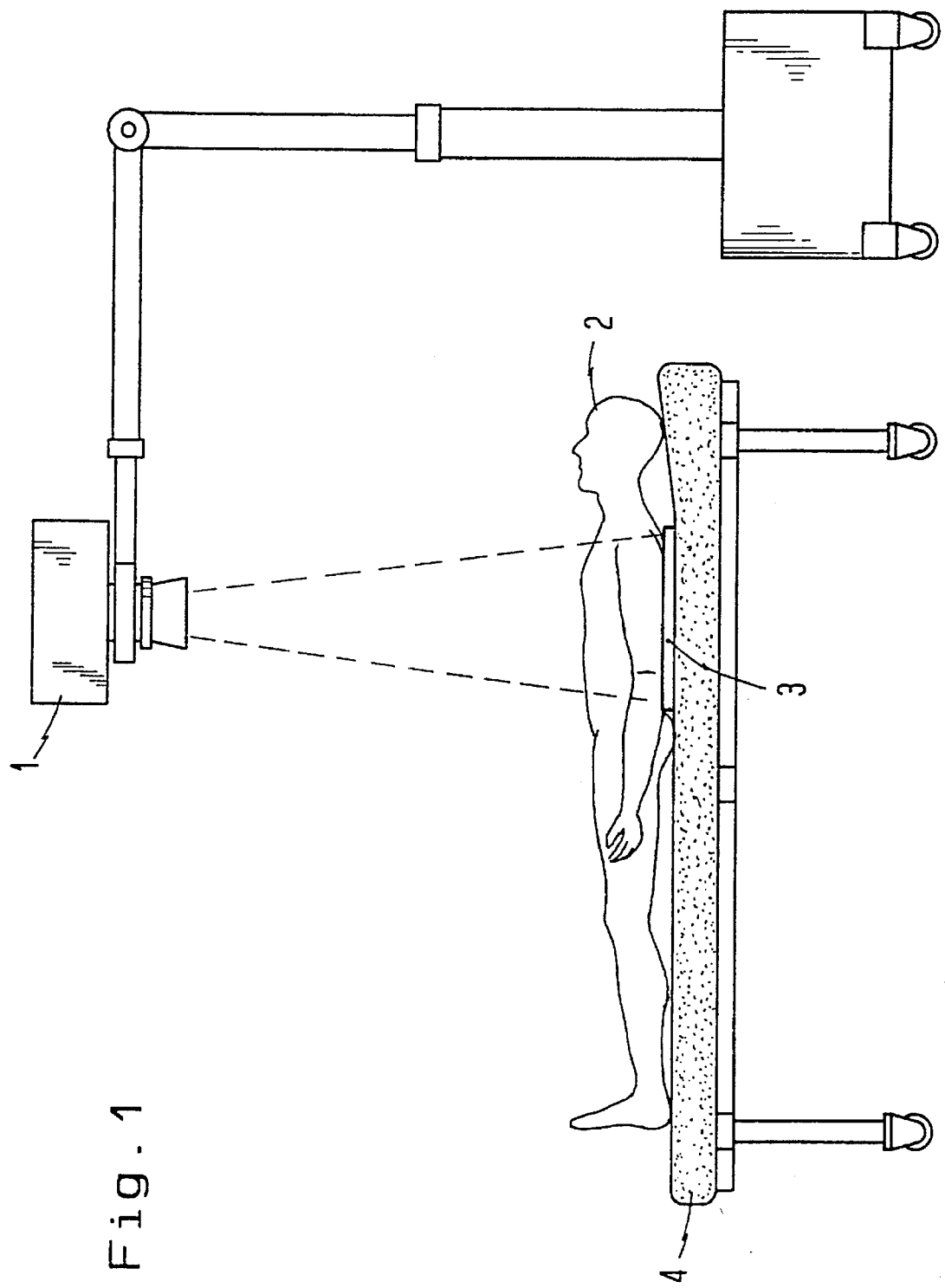
FIG. 1 is an illustration of emergency X-ray apparatus.

The preferred embodiments of the present invention will now be described with reference to FIGS. 1–6 of the drawings. Identical elements in the various figures are designated with the same reference numerals.

FIG. 1 illustrates mobile X-ray apparatus 1 of the overall type employed in emergency rooms. Apparatus 1 is positioned over a patient 2 lying on a bed 4. A lightproof holder 3 is introduced between the patient 2 and the bed 4.

Figure 2:
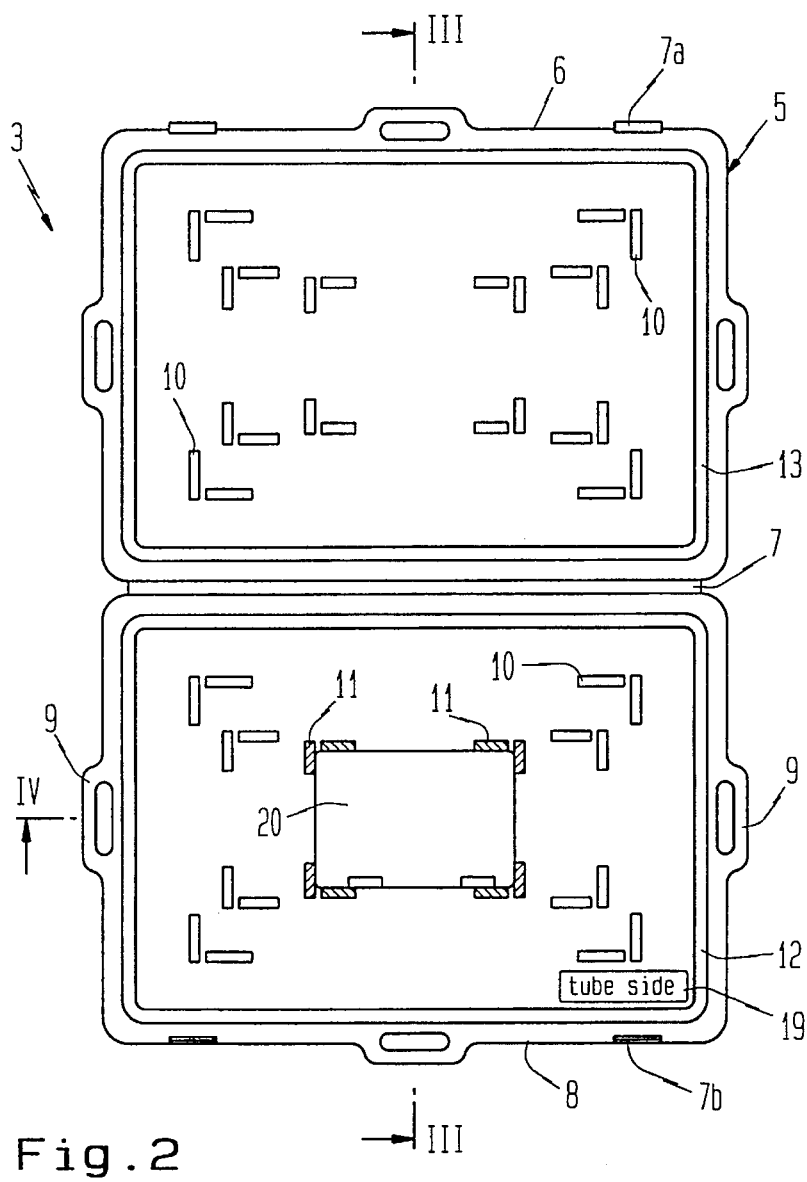
FIG. 2 illustrates a holder in accordance with the present invention.
Figure 3:
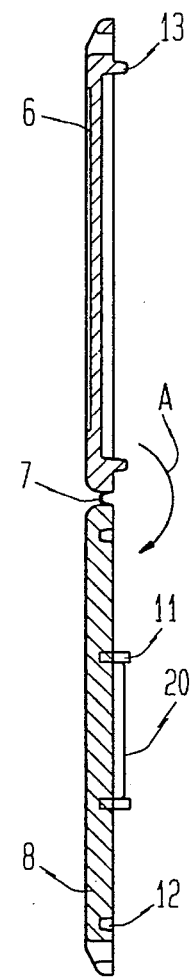
FIG. 3 is a section along the line III—III in FIG. 2.

FIG. 2 illustrates the holder 3 in the open position. It comprises an outer cassette 5 and an inner cassette 20. The outer cassette 5 has a top 6, a hinge 7, and a bottom 8. It is blow molded in one piece, preferably of polyethylene or polypropylene. The outer cassette 5 is accordingly light in weight, absorbs very few X-rays, and is relatively inexpensive to manufacture. The outer surface of the outer cassette 5 is smooth and low-friction and has no edges or grooves. It is accordingly easy to clean or disinfect. It opens and closes about the hinge 7. It has two finger grips 9, one on top 6 and the other on the bottom 8. The finger grips on top 6 match those on the bottom 8. The finger grips 9 on the top coincide with those on the bottom while the outer cassette 5 is closed. The outer cassette 5 is maintained closed by fasteners 7a on the top 6 and 7b on the bottom 8. These fasteners can be any type of luggage fastener, e.g. catches, magnetic fasteners, etc. Separate strips 11 of material can be inserted edge-down in depressions 10 in the top 6 and bottom 8. The depressions represent the outlines of the different inner cassettes that can be accommodated. The largest inner cassette that can be accommodated is 35×43 cm. The edges are centered around the center of the top 6 and bottom 8. Strips 11 completely occupy the depressions 10 in both the top 6 and the bottom 8 while the outer cassette 5 is closed. The capacity of the closed outer cassette 5 is larger than that of the inner cassette 20. The bottom 8 is identified by the words "TUBE SIDE" at a location 19 on its inner surface. The inner surface of the top 6 is surrounded by a wedge-shaped elevation 13. While the outer cassette 5 is closed, the elevation 13 fits into a matching groove 12 around the inner edge of bottom 8. The elevation 13 and groove 12 are particularly evident from FIG. 3. The holder 3 closes in the direction indicated by arrow A.

The inner cassette 20 is introduced into the outer cassette 5 between and against the strips 11. The bottom of the inner cassette 20 faces the bottom 8 of the outer cassette 5.

Figure 4:
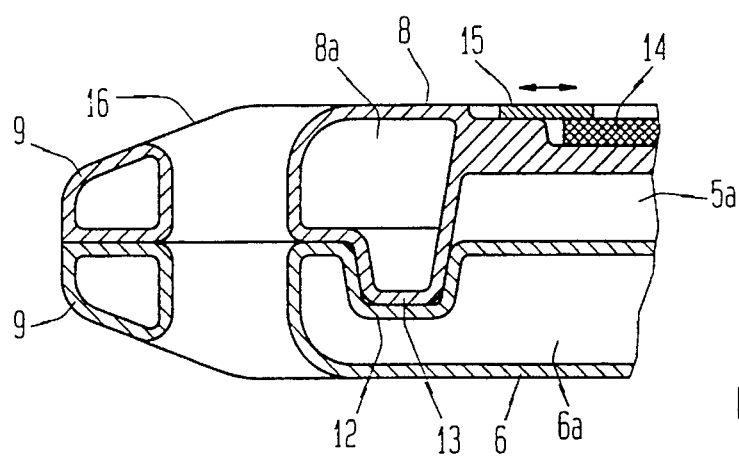
FIG. 4 is a section along the line IV in FIG. 2.

FIG. 4 is a larger-scale detail of the outer cassette in the vicinity of finger grips 9, which are integrated into the top 6 and bottom 8. Since the edges 16 of the top 6 and the bottom 8 slope together outward, the edge of the outer cassette 5 as a whole is narrower than the rest of it. Since the outer cassette 5 is a blown molding, there are cavities 6a left in the top 6 and cavities 8a in the bottom 8. The outer cassette 5 is accordingly slightly flexible and can adapt to a certain extent to the body of the patient lying on top of it. Inside the bottom 8 of the outer cassette 5 is a scatter grid 14. The scatter grid 14 is secured to, and can be released from the outer cassette 5 by sliding fasteners 15. A scatter grid 14 can be inserted into outer cassette 5 as needed. The cavity 5a between top 6 and bottom 8 is large enough to accommodate an inner cassette 20, which is not illustrated in FIG. 4.

Figure 5:
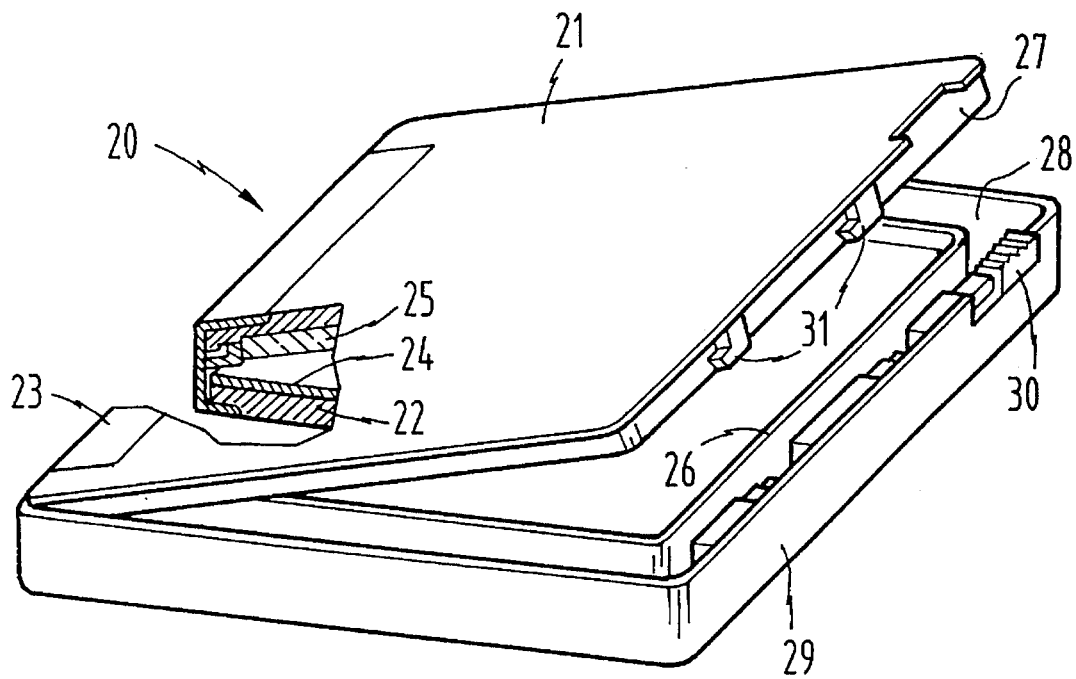
FIG. 5 illustrates a conventional X-ray cassette in a perspective and cutaway view.

FIG. 5 illustrates an inner cassette 20 in the form of a conventional cassette for holding X-ray film. The closed inner cassette 20 is light tight or "lightproof". A top 21 is attached to a bottom 22 by a hinge 23. The cassette can be opened and closed about the hinge 23. A latch operates in conjunction with hooks 31 to secure the cassette closed. A ridge 27 around the edge of the top 21 engages a light-blocking labyrinth seal 28 left on the inner surface of the bottom 22 between its outer wall 29 and a low partition 26. Both the top and bottom are provided with an image intensifying screen 25 that converts X-rays into visible light that shines, in turn, on photographic film 24. The inner cassette 20 is also plastic, although rigid enough not to yield to certain forces perpendicular to the bottom 22. This property ensures that the film 24 will rest flat against the inner cassette 20 even when subject to mechanical stress.

Figure 6:
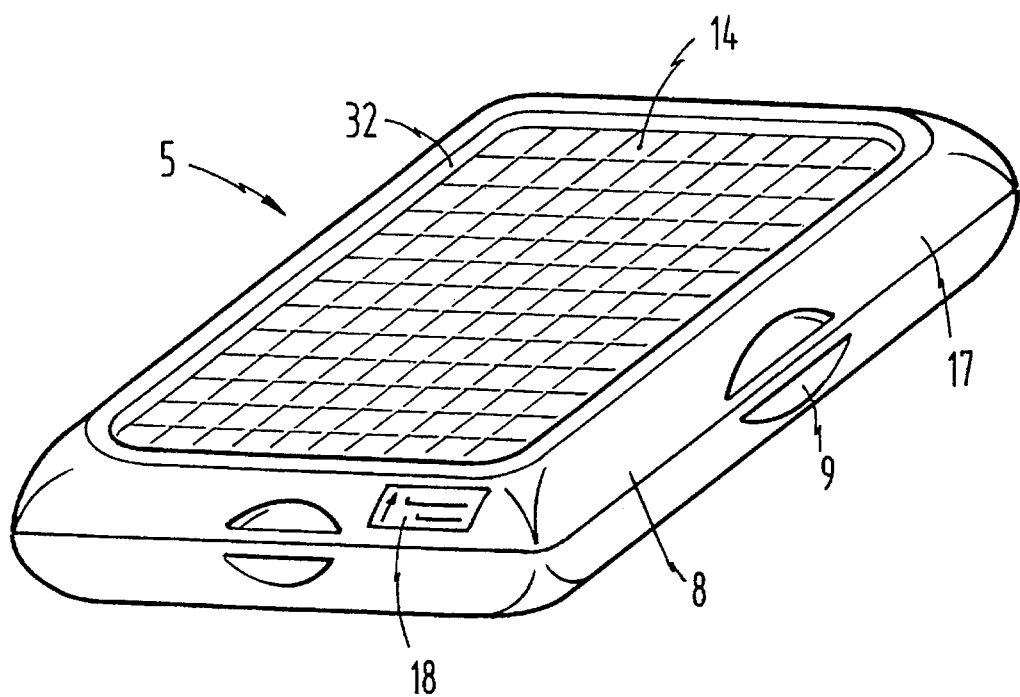
FIG. 6 is a perspective view of another embodiment of the holder illustrated in FIG. 2.

FIG. 6 illustrates another embodiment of the present invention. The finger grips 9 on the outer cassette 5 are in the form of recesses in the top 6 and bottom 8. The convex edge 17 of the outer cassette 5 slopes slightly out. Such an outer cassette 5 has even fewer sharp edges. A label 18 on the outside of the outer cassette 5 identifies the bottom 8. The scatter grid 14 in this embodiment is cemented into a recess 32 in the outer surface of bottom 8. It could just as well be accommodated in recesses in the inner surface of bottom 8 or top 6.

Scatter grids are employed in medical radiography to improve the images. The grid must be positioned at a specific distance from, and at a specific orientation to the source. Since the scatter grid 14 is positioned stationary in the outer cassette 5 during the exposure, that distance and orientation can be precisely prescribed as disclosed in the German Patent Application No. P 4 435 112.7, which is commonly assigned with the present invention.

Although only some embodiments of the present invention have been specified herein by way of example, many alternatives are possible. The outer cassette can, for example, include several recesses for scatter grids of various sizes. The grid can be secured with clips or magnets instead of a sliding grid. The outer cassette can be in several parts instead of just one. The outlines of the inner cassette in the outer cassette can be represented by frames of different size instead of by strips. The format of the outer cassette can precisely match that of the inner cassette. The outer cassette can have windows to reveal whether or not there is an inner cassette inside it.

There has thus been shown and described a novel holder for receiving a sheet-like medium for X-ray images which fulfills all the objects and advantages sought therefor. Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention, which is to be limited only by the claims which follow.

What is claimed is:

1. A holder for retaining a sheet-like X-ray sensitive medium for making X-ray pictures, said holder comprising, in combination:
   a) an inner cassette that can be opened to receive said sheet-like medium and thereafter closed, said inner cassette being lightproof when closed; and
   b) an outer cassette comprising a top, a bottom and a hinge between said top and bottom; said top, bottom and said hinge all being formed of a single piece of plastic; said top being movable with respect to said bottom by means of said hinge between an open position and a closed position; said outer cassette forming, when closed, an enclosed compartment having a low-friction shape and surface; said outer cassette having a plurality of finger grips on at least one edge and having a compartment for holding said inner cassette.

2. The holder defined in claim 1, wherein the inner cassette is accommodated loosely in the outer cassette.

3. The holder defined in claim 1, wherein the inner cassette is removably attached to the outer cassette.

4. The holder defined in claim 1, further comprising means for securing the top and bottom together and releasing them from each other.

5. The holder defined in claim 1, further comprising an image intensifying screen on at least one of the bottom and top of the inner cassette that converts X-rays into visible light.

6. The holder defined in claim 1, further comprising a plurality of depressions in at least one of the bottom and top of the outer cassette that can accommodate strips demarcating the outline of the various sizes of inner cassette that the outer cassette can accommodate.

7. The holder defined in claim 1, further comprising a mark on at least one of the inner surface and outer surface of the bottom and top of the outer cassette differentiating the bottom from the top.

8. The holder defined in claim 1, wherein the outer cassette is blow molded in one piece.

9. The holder defined claim 1, wherein the finger grips taper with the same profile toward the edge of the outer cassette.

10. The holder defined in claim 1, wherein said outer cassette is at least partly transparent.

11. The holder defined in claim 1, wherein the top and a bottom of the outer cassette interlock with each other when closed.

12. The holder defined in claim 1, further comprising a single flat depression in at least one of the top and the bottom of the outer cassette with a format that matches that of the largest inner cassette that the outer cassette can accommodate.

13. The holder defined in claim 12, further comprising means of securing a scatter grid resting in the depression.

* * * * *

UNITED STATES PATENT AND TRADEMARK OFFICE
CERTIFICATE OF CORRECTION

PATENT NO. : 5,594,774
DATED : January 14, 1997
INVENTOR(S) : Manfred Schmidt

It is certified that error appears in the above-indentified patent and that said Letters Patent is hereby corrected as shown below:

Title Page      [73] Assignee: delete "Munich" and substitute -- Leverkusen --

Signed and Sealed this

Twenty-ninth Day of April, 1997

Attest:

BRUCE LEHMAN

Attesting Officer      Commissioner of Patents and Trademarks